US008785471B2

(12) United States Patent
Sun et al.

(10) Patent No.: US 8,785,471 B2
(45) Date of Patent: Jul. 22, 2014

(54) PHARMACEUTICAL COMPOSITION CONTAINING FERULIC ACID AND MATRINE COMPOUNDS, THE PREPARATION AND THE USE THEREOF

(75) Inventors: Xiaojie Sun, Qingdao (CN); Weifu Ma, Qingdao (CN)

(73) Assignee: Qingdao Qiyuan Bio-Technologies Co., Ltd., Qingdao, Shandong (CN)

( * ) Notice: Subject to any disclaimer, the term of this patent is extended or adjusted under 35 U.S.C. 154(b) by 391 days.

(21) Appl. No.: 13/058,738

(22) PCT Filed: Sep. 9, 2009

(86) PCT No.: PCT/CN2009/073837
§ 371 (c)(1),
(2), (4) Date: Feb. 11, 2011

(87) PCT Pub. No.: WO2010/028596
PCT Pub. Date: Mar. 18, 2010

(65) Prior Publication Data
US 2011/0144143 A1 Jun. 16, 2011

(30) Foreign Application Priority Data

| Sep. 11, 2008 | (CN) | 2008 1 0304457 |
| Sep. 11, 2008 | (CN) | 2008 1 0304458 |
| Oct. 13, 2008 | (CN) | 2008 1 0304902 |
| Nov. 5, 2008 | (CN) | 2008 1 0305381 |

(51) Int. Cl.
*A61K 31/192* (2006.01)
*A61K 31/4375* (2006.01)

(52) U.S. Cl.
CPC ........... *A61K 31/192* (2013.01); *A61K 31/4375* (2013.01)
USPC ............ 514/285; 514/734; 514/731; 514/183

(58) Field of Classification Search
None
See application file for complete search history.

(56) References Cited

U.S. PATENT DOCUMENTS 6,114,377 A * 9/2000 Schnittger et al. ............ 514/461

FOREIGN PATENT DOCUMENTS

WO    WO 2008/102997 A1 * 8/2008

OTHER PUBLICATIONS

Jong et al., Using LC/MS/MS to determine matrine, oxymatrine, ferulic acid, mangiferin, and glycyrrhizin in the Chinese medicinal preparations Shiau-feng-saan and Dang-guei-nian-tong-tang, 2006, Journal of Pharmaceutical and Biomedical Analysis, vol. 40, pp. 472-477.*
International Search Report (PCT/ISA/210) issued on Dec. 17, 2009, by Chinese Patent Office as the International Searching Authority for International Application No. PCT/CN2009/073837.
Written Opinion (PCT/ISA/237) issued on Dec. 17, 2009, by Chinese Patent Office as the International Searching Authority for International Application No. PCT/CN2009/073837 (with partial English language translation).
Song Ru et al., "Study on Quality Standards for Compounds Injection of *Radix Sophorae Flavescentis*", Primary Journal of Chinese Materia Medica, 2000, vol. 14, No. 4, pp. 12-14 (with English language translation).

* cited by examiner

*Primary Examiner* — Jeffrey S. Lundgren
*Assistant Examiner* — Meghan Finn
(74) *Attorney, Agent, or Firm* — Buchanan Ingersoll & Rooney PC

(57) ABSTRACT

Preparation and usage of a pharmaceutical composition containing ferulic acid and matrine compounds are described. The ingredients ferulic acid and matrine compounds in this pharmaceutical composition have synergistic effects which can obviously improve the pharmacology effects of both the ferulic acid and matrine compounds. Moreover, the pharmaceutical composition can significantly increase the aqueous and fat solubility of the individual ingredients.

7 Claims, No Drawings

PHARMACEUTICAL COMPOSITION CONTAINING FERULIC ACID AND MATRINE COMPOUNDS, THE PREPARATION AND THE USE THEREOF

FIELD OF THE INVENTION

The present invention relates to a pharmaceutical composition containing ferulic acid and matrine compounds, the preparation methods and usage thereof.

BACKGROUND

Ferulic acid, also named as 4-hydroxy-3-methoxy cinnamic acid, is one of the phenol acids widely found in a variety of plants. Ferulic acid is one of the active ingredients in some Chinese medicinal herbs like 'Danggui' (angelica), 'Chuanxiong', and 'Awei' (ferulic) and has a wide range of pharmacology effects such as anti-inflammatory effect, antibacterial effect, anti-oxidation effect, enhancing immunity, anti-tumor effect, anti-cardiovascular disease effect, anti-thrombotic effect, anti-Alzheimer's effect, et al.

One of the most common Chinese medicinal herbs, *Sophora flavescens* Alt. contains a variety of alkaloids which mainly have matrine and oxymatrine, also have sophocarpine, sophoridine, N-oxysophocarpine and iso-matrine. Using these alkaloids like matrine, oxymatrine, and sophocarpine as active ingredients which have pharmacology effects like antivirus effect, anti-liver fibrosis effect, enhancing immunity, anti-inflammatory and antiallergic effects, some pharmaceutical products have been clinically used in the treatments for chronic liver disease, virus infection, cancer and cardiovascular disease.

Our research found that the pharmaceutical compositions containing ferulic acid and matrine compounds can significantly increase the pharmacology effects of both ferulic acid and matrine compounds, decrease the toxic effects of matrine compounds, and improve the aqueous and fat solubility of both ingredients.

DETAILED DESCRIPTION OF THE INVENTION

The present invention mainly aims to develop a pharmaceutical composition containing a combination of ferulic acid and matrine compounds which can improve the pharmacology effects of individual ferulic acid and matrine compounds.

To resolve the above mentioned technical problems, the present invention is achieved by the following embodiments:

A pharmaceutical composition containing a combination of ferulic acid and matrine compounds.

Further, the ferulic acid ingredients can comprise one or more of the following compounds: ferulic acid (structure of ferulic acid:

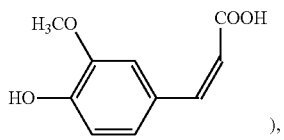

), isomer of ferulic acid (structure of iso-ferulic acid:

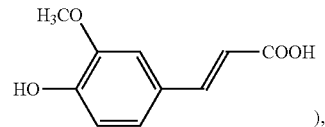 [SMILES: COc1cc(/C=C/C(=O)O)ccc1O]

), the inorganic salts of ferulic acid, and the isomers of the ferulic acid salts.

Still further, the matrine compounds have the basic quinolizin ring structure (structure:

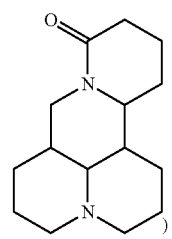 [SMILES: O=C1CCCC2C3CCCN4CCCC(CN12)C34]

)

and can comprise one or more of the following compounds: matrine, iso-matrine, oxymatrine, sophocarpine, oxysophocarpine, sophoranol, cytosine, or their isomers and inorganic salts.

Preferably, the matrine compounds can be matrine, oxymatrine, sophocarpine, or the mixture of these three compounds; and the mole ratio between ferulic acid and matrine compounds within the composition is 1:0.1~10.

Further, the matrine compounds can be matrine, oxymatrine, or the mixture of these two compounds; and the mole ratio between ferulic acid and matrine compounds within the composition is 1:0.1~10.

The second objective of the present invention is to provide a method for preparing a pharmaceutical composition containing ferulic acid and matrine compounds, in which the active ingredients are a combination of the ferulic acid and matrine compounds (the mole ratio between ferulic acid and matrine compounds within the composition is 1:0.1~10). Pharmaceutical excipient can be added to make certain types of pharmaceutical preparations by relevant pharmaceutical methods.

To make preparations for injection, water (injection grade) can be used as the pharmaceutical excipient. The active ingredients are added in the water and stirred to dissolve, to make preparations for injection.

To make oral preparations, starch, 10% starch aqueous solution, dry starch, and magnesium stearate can be used as the pharmaceutical excipients. The active ingredients are first thoroughly mixed with starch. 10% starch aqueous solution is added into the mixture to make a damp mass followed by drying. Then, the dried damp mass is mixed with dry starch and magnesium stearate to make oral preparations.

To make preparations for skin and mucous membrane, carbopol, propylene glycol, methylparaben and purified water can be used as pharmaceutical excipients. The carbopol is dispersed in purified water. The methylparaben is dissolved propylene glycol and added to the dispersed carbopol. Purified water is added into the dispersed carbopol to swell. The above mentioned combination is dissolved in the purified water and added into the swelled carbopol; purified water is added to mix uniformly, and mix them to make preparations for skin and mucous membrane.

The pharmaceutical composition containing the combination of the ferulic acid and matrine compounds can be used to prepare medicinal products for antifibrotic treatment, altering haemorheology, antivirus treatment, anti-inflammatory treatment, inhibition of cholinesterase, relieving pains and itching, anti-Alzheimer's treatment, antithrombotic treatment, antibacterial treatment, anti-tumor treatment, anti-lipid-oxidation and hypolipidemic treatment, anti-atherosclerosis treatment, antirheumatic treatment, enhancing immunity, antihypertensive treatment, and the treatment to increase the sperm motility.

Moreover, comparing to the existing art, the present pharmaceutical composition has several advantages and positive effects: the pharmaceutical composition of the present invention containing the combination of the ferulic acid and matrine compounds demonstrates significant synergistic effect, it cannot only increase the pharmacology effects of the ferulic acid compound, but also increase the pharmacology effects of the matrine compound(s). In addition, it can significantly improve the aqueous/fat solubility of both ingredients. The oral, injection and skin/mucous membrane preparations prepared from the pharmaceutical composition can prevent or treat cancer, arteriosclerosis, cardiovascular diseases, bone and joint diseases, cold, alzheimer's disease, dermatitis, eczema, acne, rash, urticaria, psoriasis, lower gastrointestinal motility, hepatitis, nephritis, organ fibrosis, acute or chronic inflammatory.

The embodiments of the invention are now illustrated in detail in connection with the drawings.

A pharmaceutical composition in the present invention is a combination of ferulic acid and matrine compounds, wherein the mole ratio between the ferulic acid and matrine compounds is 1:0.1~10, and the preferred mole ratio between the ferulic acid and matrine compounds is 1:1~5.

The ferulic acid ingredients in this invention can comprise ferulic acid [structure of ferulic acid:

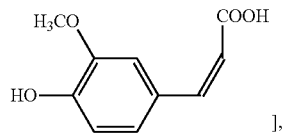 [SMILES: COc1cc(/C=C\C(=O)O)ccc1O]

], isomer of ferulic acid [structure of iso-ferulic acid:

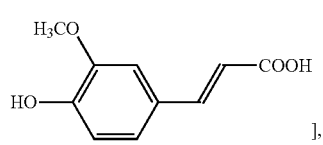 [SMILES: COc1cc(/C=C/C(=O)O)ccc1O]

], the inorganic salts of ferulic acid, and the isomers of the ferulic acid salt or a combination of two or more of these compounds. In the present invention, the matrine compound has the basic quinolizin ring structure as follows:

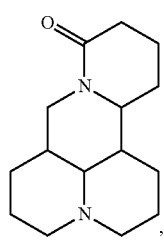 [SMILES: O=C1CCCC2C3CCCN4CCCC(CN12)C34]

, and can comprise matrine, iso-matrine, oxymatrine, sophocarpine, oxysophocarpine, sophoranol, cytosine, or their isomers and inorganic salts. Of course, it can comprise a combination of two or more of these compounds.

In a preferred embodiment, the matrine compound can be matrine, oxymatrine, sophocarpine, or the mixture of these three compounds; and the mole ratio between ferulic acid and matrine compounds within the composition is 1:0.1~10, and the preferred mole ratio between them is 1:1~3.

In another preferred embodiment, the matrine compound can be matrine, oxymatrine, or the mixture of these two compounds; and the mole ratio between ferulic acid and matrine compounds within the composition is 1:0.1~10, and the preferred mole ratio between them is 1:1~2.

When the mixture is used with a suitable pharmaceutical excipient, by using a conventional pharmaceutical method, various preparations can be prepared, such as oral, injection and skin/mucous membrane preparations, etc. The following examples describe in detail preparation of several specific different preparations.

EXAMPLE 1

Preparation of Freeze-Dried Powder Injection
Preparation of Ferulic Sodium Salt/Oxymatrine Materials: ferulic sodium 30.87 g, oxymatrine 69.13 g, water (injection grade) 1000 ml.

Preparation Methods: In a sterile operation environment, 30.87 g ferulic sodium and 69.13 g oxymatrine (mole ratio between them is 1:2) were accurately weighed and placed in a sterile container. About 100 ml water (injection grade) was added and stirred to dissolve the ingredients. The pH value of the solution was adjusted at the range of 6.5~7.5 using sodium hydroxide solution. Water (injection grade) was added to a total volume of 1000 mL. The solution was stirred uniformly. 0.02% activated carbon was added and the mixture was stirred for 5-10 minutes. The mixture was filtered by sterile filtration funnel with two layers of sterile filter paper; and further filtered with a sterile G6 sintered glass funnel. The quality of the filtrate was checked to satisfaction. The filtrate was then divided into 2 ml ampoules, freeze-dried for 24-26 hours, and then the ampoules were sealed. Each package (ampoule) contained 100 mg active ingredients.

EXAMPLE 2

Preparation of Ferulic Acid/Sophocarpine Tablet

Materials: ferulic acid 182 g (containing 60% n-ferulic acid and 40% iso-ferulic acid), sophocarpine 18 g (mole ratio between ferulic acid and sophocarpine is 10:1), starch 40 g, 10% clear starch 24 g, dry starch 23 g, magnesium stearate 3 g.

Preparation Methods: The ferulic acid and sophocarpine were sieved through 80 mesh sieve and uniformly mixed with starch. 10% clearstarch was added into the mixture to make a damp mass. The damp mass was granulated through 14 mesh sieve, dried at 70-80° C., and sieved through 12 mesh sieve. Dry starch and magnesium stearate were added to mix and pressed to make 1000 tablets. Each tablet contained 200 mg active ingredients.

EXAMPLE 3

Preparation of Ferulic Sodium/Oxymatrine Gel

Materials: ferulic sodium 6.17 g, oxymatrine 13.83 g (mole ratio between ferulic sodium and oxymatrine is 1:2), carbopol 10 g, propylene glycol 167 ml, methylparaben 0.15 g and purified water 1000 ml.

Preparation Methods: The carbopol was dispersed with 20 ml purified water. Methylparaben was dissolved in the propylene glycol and then added to the dispersed carbopol. 500 ml purified water was added into the mixture to swell for 12 to 24 hours. The ferulic sodium and oxymatrine were dissolved in 100 ml purified water and then added into the carbopol solution. Purified water was added into the mixture to a total volume of 1000 ml, and mixed uniformly. The pH was adjusted to 6.5-7.5 by ammonia water. The qualified gel was packed into aluminum tubes, each tube contained 20 g gel.

EXAMPLE 4

Preparation of Ferulic Acid/Sophora Alkaloids Capsule

Materials: ferulic acid 50 g, sophora (*Sophora flavescens* Alt.) extracts 450 g (total 60%-80% sophora alkaloids which comprise 20-30% oxymatrine, 30-60% matrine, 10-20% sophocarpine, 1-3% other alkaloids), starch 40 g, 10% clearstarch 24 g, magnesium stearate 3 g.

Preparation Methods: the ferulic acid and sophora (*Sophora Flavescens* Alt.) extracts were sieved through 80 mesh sieve and mixed with starch. 10% clear starch was added to make a damp mass. The damp mass was granulated through 14 mesh sieve, and dried at 70-80° C. The granulations were sieved through 12 mesh sieve, then uniformly mixed with dry starch and magnesium stearate. The mixture was filled into No. 3 hard gelatin capsules and capped to make total 1000 capsules. Each capsule contained 50 mg ferulic acid and 450 mg sophora alkaloids.

EXAMPLE 5

Several pharmacological experiments were performed to test the analgesic, anti-inflammatory and anticholinesterase effects of several compositions with combined ferulic acid/matrine compounds (testing groups) in comparison with the effects of individual ferulic acid or matrine compounds (control groups).

Table 1 lists the formulations of five testing compositions containing ferulic acid/matrine compounds.

TABLE 1

Five testing compositions containing ferulic acid/matrine compounds.

| Composition No. | Ferulic acid (moles) | Matrine (moles) | Oxymatrine (moles) | Sophocarpine (moles) |
|---|---|---|---|---|
| I | 1 | 1 | 0 | 0 |
| II | 1 | 2 | 0 | 0 |
| III | 1 | 1 | 1 | 0 |
| IV | 1 | 0 | 1 | 0 |
| V | 1 | 0 | 0 | 2 |

Method: Healthy mice were selected, each group containing 10 mice. The mice were intragastric administrated with 20 mg/kg testing compositions or control compositions for consecutive 3 days. 30 minutes after the last administration, the mice were intra-peritoneally (ip) injected with 10 ml/kg of 0.6% acetic acid. The writhing numbers of the mice within 15 minutes were recorded. The analgesic percentage was calculated.

Analgesic percentage(%)=(writhing numbers of blank control group−writhing numbers of testing group)/writhing numbers of blank control group×100%

Table 2 compares the analgesic effects of five testing compositions with control ferulic acid or oxymatrine.

TABLE 2

Analgesic effects of five compositions and control ferulic acid or oxymatrine.

| Groups | N (Number of Mice) | Analgesic percentage (%) |
|---|---|---|
| Blank control | 10 | — |
| Oxymatrine | 10 | 29.98 |
| Ferulic acid | 10 | 18.30 |
| I | 10 | 88.86 |
| II | 10 | 98.29 |
| III | 10 | 87.42 |
| IV | 10 | 99.36 |
| V | 10 | 78.13 |

The following are anti-inflammatory effect of several compounds in comparison with ferulic acid and oxymatrine.

Methods: formulations of five testing composition are listed in Table 1. Healthy mice were selected, each group containing 10 mice. After weighing and marking, the right ear of the mice was contacted with xylene cotton ball for 5 seconds, leaving the left ear as control. 10 minutes after proinflammatory treatment, the right ear was coated with testing compositions (1%), control ingredients (individual ferulic acid or oxymatrine) or blank control (physiological saline). 30 minutes later, the mice was sacrificed by cervical dislocation. The same volume of tissues was collected from left ear (control) and fight ear (treated with xylene) by hole puncher (diameter: 6 mm), and weighed. The ear swelling percentage was calculated.

Ear swelling percentage (%)=(Weight of right ear−Weight of left ear)/Weight of left ear×100%

Results are listed in Table 4.

TABLE 4

Anti-inflammatory effect (ear swelling percentage) of five testing compositions and individual control ingredients (ferulic acid or oxymatrine)

| Groups | Ear swelling percentage (%) |
|---|---|
| Blank control | 173.72 |
| Oxymatrine | 133.4 |
| Ferulic acid | 164.6 |
| I | 74.9 |
| II | 98.9 |
| III | 36.4 |
| IV | 111.2 |
| V | 96.7 |

The following are the effects on the proliferation and type I collagen content of hepatic stellate cells.

Materials and reagents: ELISA kit for rats type I collagen, trypsin, fetal bovine serum, etc.

Methods: Revived hepatic stellate cell (HSC) seeds were placed in a 100 ml plastic incubation flask and incubated in a $CO_2$ incubator (inside 5% $CO_2$, 95% humidity). The medium was discarded when the cells grew into a single layer. Digestion solution (5% trypsin) was added. The digestion solution was removed and centrifuged at 2200 rpm for 7 minutes. The supernatant was discarded, washed and centrifuged with DMEM incubation solution. The cells were suspended in a DMEM solution containing 20% fetal bovine serum, and the cell numbers were counted. The cell suspension was diluted with a DMEM solution and seeded in 96 well culture plate, each well having 100 μl diluted suspension. After 48 hours, the solution was removed and the cells were washed with a DMEM incubation solution containing 10% bovine serum to synchronize the cells at stable phrase. The cells were treated with testing compositions diluted in physiological saline (50 μmol/l). Each treatment tested 6 wells and repeated for 3 times. After 48 hours, incubation was terminated. 20 μl thiazolyl blue tetrazolium bromide (MTT) was added to each well and incubation was continued for an additional 4 hours. DMSO was added and shaked for 10 minutes. The HSC absorbance at wavelength 570 nm was measured by microplate reader. The cells were obtained and incubated by the above method. The supernatant was obtained and the type I collagen content was measured according to the instructions in the type I collagen kit.

Results are listed in Table 5.

TABLE 5

The effects of five compositions and control ingredients (individual oxymatrine or ferulic acid) on the proliferation and type I collagen content of hepatic stellate cells (Results are represented as the mean ± SD).

| Groups | Average absorbance | Type I collagen content (μg/l) |
|---|---|---|
| Blank control | 0.45 ± 0.22 | 73.55 ± 13.28 |
| Oxymatrine | 0.39 ± 0.17 | 63.42 ± 9.76 |
| Ferulic acid | 0.42 ± 0.24 | 64.36 ± 11.22 |
| I | 0.35 ± 0.09 | 34.57 ± 8.29 |
| II | 0.25 ± 0.07 | 46.92 ± 11.56 |
| III | 0.32 ± 0.06 | 36.48 ± 10.07 |
| IV | 0.28 ± 0.13 | 11.29 ± 8.55 |
| V | 0.22 ± 0.19 | 44.77 ± 6.99 |

The following is a comparison of anticholinesterase effects of several compounds.

Methods: 5 ml blood was collected from healthy rats, stored in tubes containing anticoagulants and diluted 10 times with physiological saline (ready for use). The testing compositions were diluted with physiological saline to 0, 5, 10, 20, 40, 80, 160, 320, 640 mg/l concentrations, respectively. 0.05 ml each diluted composition was pipetted into 0.5 ml diluted rats blood, mixed thoroughly and incubated at 37° C. for 1 hour. The activity of blood acetylcholinesterase was measured according to the acetylcholinesterase kit. The half inhibitory concentration (IC50) was calculated.

Results are as shown in Table 6. It can be seen from Table 6, five formulations of I to V can inhibit the acetylcholinesterase. Among those, composition III has the strongest inhibition activity.

TABLE 6

Half inhibitory concentration of (IC50) testing compositions and control ingredients on blood acetylcholinesterase

| Compositions | IC50 (mg/l) |
|---|---|
| Blank control | — |
| Oxymatrine | 735.5 |
| Matrine | — |
| Ferulic acid | — |
| Neostigmine | 365.7 |
| I | 223.4 |
| II | 86.5 |
| III | 58.8 |
| IV | 433.9 |
| V | 567.1 |

The following is a comparison of the effect of several compounds on mice gastrointestinal motility.

Materials and reagents: oxymatrine injection (Xinhua Inc., batch No.: 0306003), neostigmine methylsulfate injection (Tianfu Inc., batch No.: 0404131), atropine sulfate injection (Tianfu Inc., batch No.: 0409271), morphine sulfate controlled-release tablets (Mengdi Inc., batach No.: 04082312).

Animals and feeding environment: healthy SPF grade Kunming mice, half male, weight 18-22 g, provided by Lvye Inc., certificate No.: SYXK(LU)20030020. Every 10 mice were placed in one cage. Mice feeding was provided by Shandong experimental animal center. Experimental mice fed in barrier system with filtered air, at the room temperature of 18-22° C. and humidity at 50-60%, with 12 hours light radiation per day.

Methods: The mice were intragastric administrated with testing compositions or controls for consecutive 3 days. Before the last administration, the mice were stopped feeding and supplied with water for 16 hours. 30 minutes after the last administration, the mice were intragastric administrated with 0.2 ml 5% activated carbon suspension. 20 minutes later, the mice were sacrificed by cervical dislocation. The abdominal cavity was opened and bowel was collected from pylorus to ileocecal. The bowel was placed on a tray and straightened. The total length of small intestine was measured, as well as the advanced distance of carbon powder in the intestine from pylorus. The percentage of carbon powder propulsion was calculated by the following formula:

percentage of carbon powder propulsion=advanced distance of carbon powder/total length of small intestine×100%

Table 7 shows the effects of the compounds on the percentage of carbon powder propulsion (the mean±SD). Compared to controls, *P<0.01. p represents statistical difference; *P<0.05 means statistically obvious difference; **P<0.01 represents statistically significant difference.

TABLE 7

| Compounds | Administrative dosage (mg/kg) | Numbers | Percentage of carbon powder propulsion (mean ± SD, %) |
|---|---|---|---|
| Blank | — | 10 | 57.26 ± 9.10 |
| Oxymatrine | 10 | 10 | 58.85 ± 13.22 |
| Oxymatrine | 20 | 10 | 67.49 ± 11.68* |
| Ferulic acid | 20 | 10 | 54.33 ± 10.22 |
| Neostigmine | 4 | 10 | 68.55 ± 4.80** |
| I | 10 | 10 | 71.20 ± 8.11** |
| II | 10 | 10 | 78.54 ± 12.42* |
| III | 10 | 10 | 72.36 ± 8.77** |
| IV | 10 | 10 | 75.12 ± 13.35* |
| V | 10 | 10 | 79.01 ± 6.88** |

The following are experimental data of the acute toxicity effects of the compositions.

Methods: Healthy mice were selected, each group containing 10 mice. The mice were intragastric administrated with testing compositions or controls once; and observed for 72 hours. The deaths were recorded.

The results are in Table 8.

TABLE 8

Acute toxicity effects of the testing compositions

| Compositions | Administrative dosage (mg/kg) | Numbers | Death cases |
|---|---|---|---|
| Matrine | 500 | 10 | 10 |
| Ferulic acid | 1000 | 10 | 0 |
| Sophocarpine | 500 | 10 | 10 |
| I | 800 | 10 | 0 |

TABLE 8-continued

Acute toxicity effects of the testing compositions

| Compositions | Administrative dosage (mg/kg) | Numbers | Death cases |
|---|---|---|---|
| II | 800 | 10 | 0 |
| III | 800 | 10 | 0 |
| IV | 800 | 10 | 0 |
| V | 800 | 10 | 0 |

The following is observation of the anti-atherosclerosis effect of the compositions.

Testing composition preparation: ferulic acid and oxymatrine were mixed in a mole ratio 1:1 to prepare a solution.

Methods: According to the method described in reference (Liu et al., 2005. Chinese journal of arteriosclerosis, 13(3): 305-308).

Test method: 140 male quails were selected and randomly separated into 7 groups: normal control group (healthy quails), modeling control group (fat arteriosclerosis model which is set up by the methods described in reference), positive control group (fat arteriosclerosis model is treated by luofatading 10 mg/kg), ferulic acid control group (tested with ferulic acid 40 mg/kg), large/medium/small dosage testing groups (10, 20, and 40 mg/kg respectively, of testing compositions). Except the normal control group, all the other 6 groups were fat arteriosclerosis models.

The quails were daily intragastric administrated with testing compositions or controls once per day for consecutive four weeks. The fourth weekend after administration, the content of serum lipid from 10 quails of each group was detected. In the end, pathological examination was conducted on the surviving quails.

Method to detect the content of serum lipid: at the end of the $4^{th}$ week after administration, feeding was stopped for 12 hours. 2 ml blood was collected from jugular vein. The serum was separated. The contents of serum cholesterol (TC) and triglyceride (TG) were measured according to an enzymatic method.

Results: The composition containing ferulic acid and oxymatrine could significantly reduce the serum TC and TG levels in the quails of fat arteriosclerosis model, and its anti-atherosclerosis effect was obviously better than ferulic acid's. See Table 9. Most quails in the model group had obvious pathological changes in the aorta, and the aortic atherosclerosis (As) degree in most cases was above grade 2. Comparatively, the aortic atherosclerosis degree of the quails in the testing group taking the composition containing ferulic acid and oxymatrine was lower, mostly below grade 1-2. See Table 10. Most arterial intima was intact under a microscope, part of which had slightly lipid infiltration containing separated foam cells.

TABLE 9

Effects of compositions containing ferulic acid and oxymatrine on the serum TC and TG levels in the quails (Results are represented as the mean ± SD).

| Groups | TC(mmol/L) | TG(mmol/L) |
|---|---|---|
| Normal control | 4.96 ± 0.88 | 0.87 ± 0.21 |
| Modeling control | 25.23 ± 5.32 | 5.66 ± 1.21 |
| Luofatading, 10 mg/kg | 10.19 ± 2.07 | 1.68 ± 0.36 |

TABLE 9-continued

Effects of compositions containing ferulic acid and oxymatrine on the serum TC and TG levels in the quails (Results are represented as the mean ± SD).

| Groups | TC(mmol/L) | TG(mmol/L) |
|---|---|---|
| ferulic acid, 40 mg/kg | 16.88 ± 6.31 | 3.52 ± 0.73 |
| testing composition, 40 mg/kg | 11.43 ± 4.38 | 1.75 ± 0.54 |
| testing composition, 20 mg/kg | 14.67 ± 5.95 | 2.87 ± 0.45 |
| testing composition, 10 mg/kg | 15.86 ± 6.67 | 2.99 ± 0.38 |

TABLE 10

Effects of compositions containing ferulic acid and oxymatrine on the aortic atherosclerosis degree of the quails

| Groups | Numbers of quails in different the aortic atherosclerosis degree | | | | | Total atherosclerosis score |
|---|---|---|---|---|---|---|
| | 0 | 1 | 2 | 3 | 4 | |
| Normal control | 3 | 14 | 0 | 0 | 0 | 14 |
| Modeling control | 0 | 1 | 2 | 5 | 7 | 48 |
| Luofatading, 10 mg/kg | 0 | 6 | 8 | 2 | 0 | 28 |
| Ferulic acid, 40 mg/kg | 1 | 4 | 6 | 3 | 0 | 25 |
| Testing composition, 40 mg/kg | 3 | 6 | 5 | 1 | 0 | 19 |
| Testing composition, 20 mg/kg | 4 | 7 | 3 | 2 | 0 | 19 |
| Testing composition, 10 mg/kg | 2 | 5 | 7 | 2 | 0 | 25 |

The following are the effects of ferulic acid/matrine on acute rheumatoid arthritis.

Testing composition preparation: The gel containing ferulic acid and matrine (mole ratio 1:1) were prepared according to a pharmaceutical method.

Methods: 30 pairs of rheumatoid arthritis patients; 30 patients participating in the control group with daily administration of 200 mg naproxen tablets; 30 patients participating in the testing group with daily application on the affected parts of the testing gel containing ferulic acid and matrine. Both groups were administered for consecutive 5 days.

Effect observations: obviously effective if both swelling and aches disappear; effective if aches disappear with limited swelling; invalid if both swelling and aches exist.

Results: In the testing group, 21 cases were obviously effective and 8 cases were effective, total effective percentage 96.7%; in the control group, 12 cases were obviously effective and 11 cases were effective, total effective percentage 76.7%.

The following are the effects of several compounds on rash.

Patient selection: 18-25 years old of either gender with rash at both body sides. Each composition was tested on 10 patients. Test was carried out with single-blind and self control. 1% composition or control was applied on rash area at left side of the body, and physiological saline was applied on rash area at the right side. After 10 minutes, the effects were evaluated.

Effect evaluation: Obviously effective if both rash and itching feeling disappear; effective if parts of rash and itching feeling disappear; invalid if both rash and itching feeling keep unchanged.

Results are as shown in Table 11.

TABLE 11

The effects of the composition on rash

| Composition | Obviously effective | Effective | Invalid |
|---|---|---|---|
| Oxymatrine | | 10 | |
| Ferulic acid | | 3 | 7 |
| I | 10 | | |
| II | 8 | 2 | |
| III | 10 | | |
| IV | 10 | | |
| V | 10 | | |

The following are the effects of compositions II, III, V on Alzheimer's disease in rats.

1. Materials and Reagents: oxymatrine, matrine and sophocarpine (Boertaili Inc., Ninxia), huperzine A tablets (Hongqi Inc., Shanghai), D-galactose (No. 2 Shanghai reagent factory), ibotenic acid (IBO, Sigma), all of analytical purity, and total cholinesterase detect kit (Jianchen Inc., Nanjin).

2. Animal grouping, modeling and administration: 57 female Wistar rats (15 month old, 300-450 g, from animal center of Qingdao Institute for Drug Control, fed under normal conditions and natural light with unlimited drink and food) were randomly separated into 6 groups. Rats in normal control group were intraperitoneal injected with physiological saline for 6 weeks and injected physiological saline into the meynert nucleus basalis. Rats in modeling control group were injected intraperitoneally with D-galactose (48 mg/kg/d) for 6 weeks and injected with ibotenic acid into the meynert nucleus basalis. Rats in huperzine A control group and testing groups were treated in the same manner as the modeling control group. After modeling, the rats in the huperzine control group were intragastrically administrated with huperzine A tablets (50 μg/kg). The rates in testing groups II, III, V were intragastrically administered with composition (50 mg/kg). The rats in the normal and modeling control groups were intragastrically administrated with physiological saline for consecutive 7 days. 1 hour after the last administration, the learning ability of all the rats; was evaluated. Then, the rats were anesthetized with Pentobarbital. 5 ml blood was collected from abdominal aorta. Immediately the cortex tissue was collected and homogenated with physiological saline into 10% (W/N). The AChE activity in cortex tissue and blood was measured according to the reagent kit instructions.

3. Measurement: testing the memory ability of rats: the rats were placed in an electric box with an escaping platform for 3 minutes to get used to the new environments. The box was then connected to 50V AC. Upon being shocked, the rats can escape the electricity by jumping onto the platform. The shocked times (mistakes) within 5 minutes were recorded as a reference for the learning ability of the rats. After 24 hours, the rats were placed directly on the platform. The latency time for the first jump was recorded as a reference for the memory ability. The shocked times (mistakes) within 5 minutes were also recorded. The latency time of over 5 minutes was considered as 5 minutes.

T testing method was used to evaluate the difference within different groups, and the difference was statistically significant when $P<0.05$.

4. Results: The AChE activity in cortex tissue and blood can be reduced in the testing group II, III, V. As well, the learning and memorizing ability of rats were improved. See Tables 12, 13. Comparing to the modeling groups, $P<0.05$; **$P<0.01$. P represents statistic difference. *$P<0.05$ means statistically obvious difference, **$P<0.01$ statistically significant difference.

TABLE 12

The effects of compositions II, III, V on the AChE activity in cortex tissue and blood.

| Groups | N | Blood TchE (mmol/L) | Inhibition percentage | Cortex TchE (μmol/g) | Inhibition percentage |
|---|---|---|---|---|---|
| Normal control | 10 | 76 ± 28 | — | 3.4 ± 0.7 | — |
| Modeling control | 10 | 84 ± 32 | — | 3.8 ± 0.9 | — |
| Huperzine A control | 8 | 48 ± 35* | 42.86% | 2.0 ± 0.6* | 41.18% |
| II | 10 | 37 ± 29* | 55.95% | 1.4 ± 0.7** | 58.82% |
| III | 9 | 26 ± 35* | 69.05% | 1.6 ± 0.8** | 52.94% |
| V | 10 | 33 ± 27* | 60.71% | 1.8 ± 0.9** | 47.06% |

(*$P<0.05$, **$P<0.01$, in comparison with the modeling control, results are represented as the mean ± SD)

TABLE 13

The effects of compositions II, III, V on the learning and memorizing ability of rats in the jumping tests.

| Groups | Mistakes within 5 min | Latency(s) | Mistakes within 5 min after 24 hours |
|---|---|---|---|
| Normal control | 0.9 ± 0.7 | 237 ± 86 | 0.3 ± 0.2 |
| Modeling control | 16 ± 7.6 | 78 ± 27 | 9 ± 4.2 |
| Huperzine A control | 4 ± 2.3* | 135 ± 55* | 2 ± 1.6* |
| II | 5 ± 1.9* | 187 ± 43* | 4 ± 2.1* |
| III | 3 ± 2.2* | 222 ± 78* | 3 ± 1.0* |
| V | 4 ± 2.7* | 112 ± 41* | 2 ± 1.5* |

(*$P<0.05$, in comparison with the modeling control, results are represented as the mean ± SD)

In summary, this invention has been described by reference to the above preferred examples. However, it may be embodied in other specific forms or variations thereof without departing from its special or essential characteristics. The examples described above are therefore considered to be illustrative in all respects and not restrictive, the scope of the invention being indicated by the relative claims rather than by the foregoing description.

What is claimed is:

1. A pharmaceutical composition for oral or topical administration consisting of a combination of ferulic acid and matrine compounds, wherein said matrine compound consists of either oxymatrine or a combination of oxymatrine and matrine, and wherein a mole ratio between the ferulic acid and matrine compounds within the composition is 1:0.1 to 1:10.

2. The composition as claimed in claim 1, wherein any of the ferulic acid, oxymatrine or matrine are present as an inorganic salt.

3. A method of preparing a pharmaceutical composition for oral or topical administration, wherein the pharmaceutical composition consists of a combination of ferulic acid and matrine compounds, and a pharmaceutical excipient, wherein said matrine compound consists of either oxymatrine or a combination of oxymatrine and matrine, the method comprising adding a pharmaceutical excipient to the ferulic acid and matrine compounds to produce a pharmaceutical preparation, wherein the mole ratio of ferulic acid to matrine compounds in the composition is between 1:0.1 to 1:10.

4. The method as claimed in claim 3, wherein the pharmaceutical excipient is selected from the group consisting of water, starch, magnesium stearate, carbopol, propylene glycol and methylparaben.

5. A pharmaceutical composition for oral or topical administration consisting an active ingredient consisting of a combination of ferulic acid and matrine compounds, and a pharmaceutical excipient, wherein said matrine compound consists of either oxymatrine or a combination of oxymatrine and matrine, and wherein a mole ratio between the ferulic acid and matrine compounds within the composition is 1:0.1 to 1:10.

6. The composition as claimed in claim 5, wherein any of the ferulic acid, oxymatrine or matrine are present as an inorganic salt.

7. The composition as claimed in claim 5, wherein the pharmaceutical excipient is selected from the group consisting of water, starch, magnesium stearate, carbopol, propylene glycol, and methylparaben.

* * * * *